United States Patent [19]

Tytell et al.

[11] 4,198,479

[45] Apr. 15, 1980

[54] REPLACEMENT OF ANIMAL SERUM PROTEINS BY HUMAN ALBUMIN FOR GROWTH AND INTERFERON PRODUCTION BY NAMALVA CELLS

[75] Inventors: Alfred A. Tytell; Edgar Scattergood, both of Lansdale; Arthur K. Field, North Wales, all of Pa.

[73] Assignee: Merck & Co., Inc., Rahway, N.J.

[21] Appl. No.: 25,305

[22] Filed: Mar. 30, 1979

[51] Int. Cl.$^2$ .................... A61N 1/02; A61K 45/02
[52] U.S. Cl. ............................................. 435/2; 424/85
[58] Field of Search ........................... 195/1.8; 424/85

[56] References Cited

U.S. PATENT DOCUMENTS 3,800,035  3/1974  Goore .................................... 424/85
3,951,740  4/1976  Gresser et al. ........................ 195/1.8

OTHER PUBLICATIONS

Reizin et al–Chem. Abst. vol. 84 (1976) p. 103,728g.

*Primary Examiner*—Sam Rosen
*Attorney, Agent, or Firm*—Hesna J. Pfeiffer; Julian S. Levitt; Harry E. Westlake

[57] ABSTRACT

The invention provides an improved process for the growth of lymphoblastoid cells in a medium supplemented with human albumin. The invention further provides for the production of interferon by viral infection of these lymphoblastoid cells in a medium also supplemented with human albumin. This invention eliminates the necessity for adding animal proteins.

4 Claims, No Drawings

REPLACEMENT OF ANIMAL SERUM PROTEINS BY HUMAN ALBUMIN FOR GROWTH AND INTERFERON PRODUCTION BY NAMALVA CELLS

BACKGROUND OF THE INVENTION

This invention relates to the improved manufacture of preparations rich in interferon. Interferon is a protein synthesized by cells in response to induction by viruses or other substances. To date, sufficient clinical evidence of the potential therapeutic value of interferon has been gathered to generate some optimism that interferon may become an important antiviral and/or anti-tumor agent. Interferon is specific in protecting primarily the cellular species in which it has been produced. For protecting human cells in vitro it is, therefore, important to employ an interferon produced by human cells. Accordingly, human leukocyte cells have been the most commonly used cells for the production of human interferon.

The therapeutic value of interferon has not been sufficiently explored because considerable difficulties have been encountered in mass production. For the large scale clinical trial required to sufficiently evaluate the therapeutic potential of human interferon, a more dependable and economical source than human luekocytes has been developed. This source is the lymphoblastoid cell (e.g., Namalva), a rapidly growing transformed lymphocyte capable of producing high titered interferon. Namalva interferon is similar to that produced by human leukocytes, thus providing a practical means of large scale production without relying on freshly harvested blood leukocytes. However, at present, Namalva cell interferon is produced in media containing calf serum proteins, making mandatory the removal of the extraneous animal blood proteins by extensive purification.

According to the present invention, the problem of contamination by non-human serum proteins is avoided. It has been found that human albumin can replace animal serum proteins for both the growth phase and the interferon production phase of Namalva cells.

SUMMARY OF THE INVENTION

The development of a practical system for production of large quantities of human interferon is essential if interferon therapy is to become an important contribution to human medicine. By far, the most economical system presently under consideration involves growth and induction of lymphoblastoid cells. However, major obstacles to large scale production of clinically acceptable interferon still exist; one of which is interferon contaminated with proteins of non-human origin. According to the present invention, the major contributor to contamination, animal serum proteins, has been eliminated. According to the present invention, growth of Namalva cells and production of high yields of human interferon are accomplished using media in which animal serum proteins are totally replaced by human albumin.

According to the present invention, Namalva cells have been successfully grown by repeated passage, using media with complete replacement of fetal calf serum by human albumin. Interferon yields from human albumin grown cells were comparable to yields from calf serum grown cultures. Cell growth and interferon production were comparable using media containing 10% fetal calf serum or 0.15 to 0.3% human albumin. Namalva cells grown and induced in media containing human albumin instead of calf serum produced high interferon titers (up to $10^4$ units/$10^6$ cells/ml).

The human albumin used in the present invention may be prepared by various methods known in the prior art. For example, by differential precipitation of the proteins of plasma or serum with salts such as sodium or ammonium sulfates at high concentration. A technique for fractionating human serum and crystallizing human plasma albumin has been described based on the control of ammonium sulfate concentration and pH in F. E. Kendall, J. Biol. Chem. 138, 97(1941). The widely used Cohn low temperature-ethanol procedures have been described and reviewed in E. J. Cohn, et al., 1946, J.A.C.S., 68:459; Oncley, J.L., et al., 1949, J.A.C.S., 71:541; and Strong, L.E., 1948, Blood Fractionation, Vol. 2, Kirk-Othmer Encyclopedia of Chemical Technology, Interscience Encyclopedia, Inc. The crystallization of human plasma albumin using sodium sulfate and sodium potassium phosphate is described in Haupt, H., and K. Heide, 1967, Klin, Wochenschr., 45(14): 726. A system for fractionating plasma proteins by utilization of protein-metal ion interactions was described in Cohn, E.J., et al., 1950, J.A.C.S., 72:465; A system for fractionating plasma proteins by utilization of protein-metal ion interactions is described in Tage Astrup et al., Acta Chem. Scand. 8, 1361 (1954) and F.R.W. Gurd et al., 1957, J.A.C.S., 76:187. Techniques for the fractionation of plasma and purification of albumin on cellulose ion exchangers have been described by Hartley, R. W., Jr., E. A. Peterson, and H. A. Sober, 1962, Biochemistry, 1:60; Sober, H. A., F. J. Cutter, M. M. Wyckoff, and E. A. Peterson, 1956, J.A.C.S., 78:756. Gel chromatography, calcium phosphate chromatography and partition chromatography can also be adapted for large scale preparation of human albumin. Regardless of the method used for preparing human albumin, it should be such that it can be used for parenteral injection in humans.

PREFERRED EMBODIMENTS

EXAMPLE 1

Growth of Human Lymphoblastoid (Namalva) Cells and Interferon Production in Culture Media Containing 0.3% Human Albumin (Albumisol[R])

Step 1—Namalva Cell Growth

Viable human lymphoblastoid cells (Namalva) were obtained from Dr. K. C. Zoon, Laboratory of Chemical Biology, National Institute of Arthritis, Metabolism and Digestive Diseases, National Institutes of Health, Bethesda, Md. 20014. The cells were routinely maintained and subcultured in roller bottles at 37° C. in synthetic Medium RPMI 1640 (manufactured by Grand Island Biological Company, Grand Island, N.Y.). The RPMI 1640 medium was developed at Roswell Park Memorial Institute for growing human and mouse leukemia cells. Said medium contains the following components:

| Component | mg/L |
| --- | --- |
| Inorganic Salts | |
| $Ca(NO_3)_2 \cdot 4H_2O$ | 100.00 |
| KCl | 400.00 |
| $MgSO_4 \cdot 7H_2O$ | 100.00 |
| NaCl | 6000.00 |
| $NaHCO_3$ | 2000.00 |
| $Na_2HPO_4 \cdot 7H_2O$ | 1512.00 |

| Component | mg/L |
|---|---|
| Other Components | |
| Glucose | 2000.00 |
| Glutathione (reduced) | 1.00 |
| Phenol Red | 5.00 |
| Amino Acids | |
| L-Arginine (free base) | 200.00 |
| L-Asparagine | 50.00 |
| L-Aspartic acid | 20.00 |
| L-Cystine | 50.00 |
| L-Glutamic acid | 20.00 |
| L-Glutamine | 300.00 |
| Glycine | 10.00 |
| L-Histidine (free base) | 15.00 |
| L-Hydroxyproline | 20.00 |
| L-Isoleucine (Allo free) | 50.00 |
| L-Leucine (Methionine free) | 50.00 |
| L-Lysine HCl | 40.00 |
| L-Methionine | 15.00 |
| L-Phenylalanine | 15.00 |
| L-Proline (Hydroxy L-Proline free) | 20.00 |
| L-Serine | 30.00 |
| L-Threonine (Allo free) | 20.00 |
| L-Tryptophan | 5.00 |
| L-Tyrosine | 20.00 |
| L-Valine | 20.00 |
| Vitamins | |
| Biotin | 0.20 |
| D-Ca pantothenate | 0.25 |
| Choline Cl | 3.00 |
| Folic Acid | 1.000 |
| i-Inositol | 35.000 |
| Nicotinamide | 1.000 |
| Para-aminobenzoic acid | 1.000 |
| Pyridoxine HCl | 1.000 |
| Riboflavin | 0.200 |
| Thiamine HCl | 1.000 |
| Vitamin $B_{12}$ | 0.005 |

The Medium RPMI 1640 was supplemented with 50 μg/ml neomycin and 0.3% (weight/volume) human albumin (ALBUMISOL®) manufactured by Merck, Sharp & Dohme, Rahway, N.J.

Viable Namalva cells were seeded at $2 \times 10^5$ cells/ml into 5 liters of prewarmed 37° C. Medium 1640 in a 10 liter Bilthoven fermenter (manufactured by Contact Holland Ltd., Ridderkerk, Holland) containing 50μ g neomycin/ml and 0.3% human albumin (Albumisol®).

Cell replication, glucose concentration, culture temperature, dissolved oxygen concentration and culture pH were monitored during the incubation period. Cells were kept in suspension by constant slow stirring (60 RPM).

During the growth phase, pH was recorded and maintained at 7.1±0.1 by automatic adjustment of $CO_2$ input in the gas overlay. Temperature was controlled at 37° C.±0.5° C. and continuously recorded. Dissolved oxygen was continuously recorded and maintained at no less than 30% of the starting equilibrium value attained with an air overlay. Cell growth, viability and glucose concentration were evaluated by periodic sampling of the culture suspension.

Following a short initial lag phase exponential growth commenced and continued with doubling times of 20 hours. Termination of exponential growth occurred at approximately 4 to 5 days with a final cell density of $2 \times 10^6$ cells/ml. The culture contained at least 90% viable cells.

Step 2—Interferon Production

The culture grown as described in Step 1 was diluted with fresh Medium RPMI 1640, prewarmed to 37° C. containing human albumin (final concentration of 0.15%), to a viable cell concentration of $1 \times 10^6$ cells/ml. The culture was induced to produce interferon by addition of Sendai virus to a final concentration of 24 hemagglutinin units/$10^6$ cells. Sendai virus was obtained from Dr. K. C. Zoon, Laboratory of Chemical Biology, National Institute of Arthritis, Metabolism and Digestive Diseases, National Institutes of Health, Bethesda, Md. 20014. Virus stocks were prepared from Sendai virus infected egg allantoic fluids. The allantoic fluids were filtered to effect sterility and aliquoted. Virus stocks contained $10^4$ hemagglutinin units (HA)/ml, and were stored at −70° C.

The culture was incubated for 2 hours at 37° C. and then the temperature was decreased to 35° C. for the duration of the interferon production.

Samples (10 ml) were periodically taken from the culture during the interferon production phase. These samples were clarified free of cells by centrifugation. The pH of the supernatant was adjusted to 2.0 and the supernatant was stored at 4° C. for 24 hours to inactivate residual Sendai virus. The supernatant was assayed for interferon content by capacity to suppress vesicular stomatitis virus plaque development on monolayers of FS-4 (human foreskin) cells. Under the above conditions, peak interferon titers of up to $10^4$ interferon units/$10^6$ cells/ml were obtained. Thus, 0.3% human albumin was used in complete substitution for fetal calf serum in growth of Namalva human lymphoblastoid cells, and 0.15% human albumin was used in complete substitution for fetal calf serum for interferon production by these same cells.

The crude interferon obtained in Step 2 is partially purified by the procedure described by K. Cantell et al., J. gen. Virol. 39, 541–543 (1978). This partially purified interferon is aseptically distributed in suitable ampoules and stored at −70° C. A human dose of interferon may vary, but commonly one million units ($10^6$) is taken as a dose by injection.

What is claimed is:

1. An improved process for the preparation of interferon which comprises
   (a) growing human lymphoblastoid cells in medium for 4 to 5 days and obtaining a final cell density of about $2 \times 10^6$ cells/ml; and
   (b) diluting said culture with fresh medium to a cell density of about $1 \times 10^6$ cell/ml; and
   (c) inducing the production of interferon in the culture by the addition of Sendai virus; wherein the improvement comprises replacing animal serum proteins in the said medium in Step a) and b) by human albumin.

2. The improved process according to claim 1 wherein said improvement comprises supplementing said medium with about 0.15 to about 0.30% (weight/volume) human albumin.

3. The improved process according to claim 2 wherein said improvement comprises supplementing said media with about 0.30% (weight/volume) human albumin in Step a) and 0.15% in Step b).

4. The composition comprising Medium RPMI 1640 and about 0.15 to about 0.3% human albumin (weight/volume).

* * * * *